United States Patent [19]
Ono et al.

[11] Patent Number: 6,137,003
[45] Date of Patent: Oct. 24, 2000

[54] BIS (HALOETHYL) AMINOBENZENE DERIVATIVES

[75] Inventors: Mitsunori Ono, Lexington; Keizo Koya, Brookline, both of Mass.; Lijun Sun, Decatur, Ala.; Wojciech Wrona, Brookline, Mass.; Sylvia Holden, Woburn, Mass.; Noriaki Tatsuta, Lexington, Mass.

[73] Assignee: Shionogi BioResearch, Lexington, Mass.

[21] Appl. No.: 09/181,436

[22] Filed: Oct. 28, 1998

[51] Int. Cl.$^7$ .................................................. C07C 229/00
[52] U.S. Cl. .......................... 562/453; 562/456; 560/46; 560/47
[58] Field of Search ................... 562/453, 456; 560/46, 47

[56] References Cited

U.S. PATENT DOCUMENTS 5,852,011  12/1998  Matsunaga et al. .

FOREIGN PATENT DOCUMENTS

| | | |
|---|---|---|
| 703641 | 9/1967 | Belgium . |
| 1906709 | 2/1969 | Germany . |
| 9532960 | 12/1995 | WIPO . |

OTHER PUBLICATIONS

Abela Medici et al., "Cyctotoxic Compounds. Part 22. Reaction of 2,2'–Iminodiethanol with some Chloronitrobenzenes", J.Chem.Soc. Parkings Trans. 1, 1977, pp. 2517–2520.

Anastasiou et al., "On the Formation of Homo–azasteroidal Esters of N,N–Bis(2–chloroethyl)aminobenzoic Acid Isomers and their Antitumor Activity", J.Heterocyclic Chem., 1994, 31:367–374.

Badilescu et al., "Potential Anticancer Agents. XX. 1. Steric Fit Analysis in Aromatic Nitrogen Mustards Area", Neoplasma 1980, 27(3):261–269.

Baker et al., "Potential Anticancer Agents. LXXVIII. Nonclassical Antimetabolites. IV. Synthesis of Compounds . . . ", J.Org.Chem., 1962, 27:3283–3295.

Cambanis et al., "Potential Anticancer Agents. V. New Aromatic Nitrogen Mustards Related to 3–[N,N–Bis(2–chloroethyl)amino]–4–methylbenzoic Acid", J.Med.Chem. 1969, 12:161–164.

Elian et al., "Potential anticancer agents", Eur.J.Med.Chem.– Chim.Ther., 1983 18(4):385–387.

Everett et al., "Aryl–2–halogenoalkylamines. Part XII. Some Carboxylic Derivatives of NN–Di–2–chloroethylaniline", Journal of the Chemical Society, 1953, Part III, pp. 2386–2392.

Everett et al., "Aryl–2–halogenoalkylamines. Part II", Journal of the Chemical Society, 1949, Part III pp. 1972–1983.

Fu et al., "Synthesis and Biological Activity of Isomers of N–[Bis(2–chloroethyl)aminobenzoyl]glutamic Acid" J.Med.Chem., 1964, 7:759–762.

Fu, "para–[N–Bis–(2–chloroethyl)]–aminobenzoylglutamic Acid", J.Med.Pharm.Che., 1962, 5:33–41.

Greig et al., "Physicochemical and Pharmacokinetic Parameters of Seven Lipophilic Chlorambucil Esters Designed for Brain Penetration", Cancer Chemother Pharmacol, 1990, 25;311–319.

Niculesu–Duvaz et al., "Potential Anticancer Agents. XX. 2. Quantitative Structure–Activity Relationships (QSAR) in Aromatic Nitrogen Mustards Area", Neoplasma 1980 27(3):271–278.

Niculescu–Duvaz et al., "Potential Anticancer Agents. VI New Aromatic Nitrogen Mustards with Good Antitumor Activity", Revue Roumaine de Chimie, 1969, 14:535–547.

Niculescu–Duvaz et al., "Potential Anticancer Agents. IV. Nitrogen Mustards of Methylbenzoic Acids", J.Med.Chem., 11:500–503, 1968.

Pairas et al., "A New Route for the Synthesis of Steroidal Esters of Carboxylic Derivatives of N,N–bis(2–chloroethyl) aniline with DCC", Eur. J.Med.Chem.–Chim.Ther., 1985, 20(3):287–288.

Palmer et al., "Hypoxia–Selective Antitumor Agents . . . ", J.Med.Chem. 1996, 39:2518–2528.

Palmer et al., "Reductive Chemistry of the Novel Hypoxia–Selective Cytotoxin 5–[N,N–Bis(2,chloroethyl)amino]–2–4,dinitrobenzamide", J.Med.Chem., 1995, 38:1229–1241.

Palmer et al., "Hypoxia–Selective Antitumor Agents. 9. Structure–Activity Relationships for Hypoxia–Selective Cytotoxicity . . . ", J.Med.Chem., 1994, 37:2175–2184.

P'an et al., "Tumor chemotherapy. II. Synthesis of nitrogen mustards related to local anesthetics . . . " Chem. Abstr., 1960, 18420.

P'an et al., "Tumour Chemotherapy II", SciSin(Engl.Ed.), 1960, 9:89–98.

Popp, "The Reaction of N,N–Bis(2–chloroethyl)amines with Hydrazine", J.Org.Chem., 1963, 28:580–581.

Springer et al., "Novel Prodrugs of Alkylating Agents from 2–Fluoro– and 3–Fluorobenzoic Acids for Antibody–Directed Enzyme Prodrug Therapy", J.Med.Chem., 1994, 37:2361–2370.

*Primary Examiner*—Paul J. Killos
*Attorney, Agent, or Firm*—Fish & Richardson P.C.

[57] ABSTRACT

The present invention relates to bis(haloethyl)aminobenzene derivatives featured by having carboxyl-containing moiety and one other moiety at the ortho position with respect to the bis(haloethyl)amino substituent of the benzene ring. The moiety at the ortho position can be alkyl, cycloalkyl, heterocycloalkyl, aryl heteroaryl, alkyl(cycloalkyl), alkyl (heterocycloalkyl), alkyl(heteroaryl), alkyl(aryl), —(—O-alkyl)$_{2-5}$ or —Y$^1$—Y$^2$ in which Y$^1$ is O, S, or N(R$^5$) wherein R$^5$ is hydrogen or alkyl, and Y$^2$ is alkyl, alkenyl, cycloalkyl, heterocycloalkyl, aryl, heteroacryl, alkyl(cycloalkyl), alkyl (hetero-cycloalkyl), alkyl(aryl), or alkyl(heteroaryl).

30 Claims, No Drawings

BIS (HALOETHYL) AMINOBENZENE DERIVATIVES

BACKGROUND OF THE INVENTION

Cancer is the second leading cause of death in the United States. According to the American Cancer Society, there has been a steady rise in the cancer mortality rate in the United States during the past half-century. 4 millions people have died from cancer since the turn of this decade. Among all types of cancer treatment, e.g., chemotherapy, immunotherapy, surgery, radiation, and hormone therapy, chemotherapy is the most commonly employed treatment, especially for cancers that are in inoperable or metastatic forms.

Although many compounds are now known to be effective chemotherapeutics for treating cancers, there still exists a need for more potent and selective anticancer drugs.

SUMMARY OF THE INVENTION

An aspect of this invention relates to a bis(haloethyl) aminobenzene derivative wherein the para position with respect to the bis(haloethyl)amino substituent of the benzene is substituted with —C(=O)—O—$R^1$—$R^2$. $R_1$ is $C_{1-5}$ alkyl (divalent), or deleted. $R^2$ is hydrogen, $C_{3-10}$ cycloalkyl, 3- to 10-membered heterocycloalkyl, $C_{6-12}$ aryl, 5- to 12-membered heteroaryl, or —N($R^3$)$R^4$ in which each of $R^3$ and $R^4$, independently, is hydrogen, $C_{1-5}$ alkyl, $C_{3-10}$ cycloalkyl, 3- to 10-membered heterocycloalkyl, $C_{6-12}$ aryl, or 5- to 12-membered heteroaryl.

One and only one of the two ortho positions with respect to the bis()haloethyl)amino substituent of the benzene is substituted with $C_{2-18}$ alkyl, $C_{3-10}$ cycloalkyl, 3- to 10-membered heterocycloalkyl, $C_{6-12}$ aryl, 5- to 10-membered heteroaryl, $C_{1-5}$ alkyl($C_{3-10}$ cycloalkyl), $C_{1-5}$ alkyl(3- to 10-membered heterocycloalkyl), $C_{1-5}$ alkyl(5- to 10-membered heteroaryl), $C_{1-5}$ alkyl($C_{6-12}$ aryl), —(—O—$C_{1-5}$ alkyl)$_{2-5}$ or —$Y^1$—$Y^2$ in which $Y^1$ is O, S, or N($R^5$) in which $R^5$ is hydrogen or $C_{1-5}$ alkyl, and $Y^2$ is $C_{1-18}$ alkyl, $C_{2-18}$ alkenyl, $C_{3-10}$ cycloalkyl, 3- to 10-membered heterocycloalkyl, $C_{6-12}$ aryl, 5- to 10-membered heteroaryl, $C_{1-5}$ alkyl($C_{3-10}$ cycloalkyl), $C_{1-5}$ alkyl(3- to 10-membered heterocycloalkyl), $C_{1-5}$ alkyl($C_{6-12}$ aryl), or $C_{1-5}$ alkyl(5- to 10-membered heteroaryl).

Each of the remaining positions of the benzene, independently, is unsubstituted or substituted with -$Z^1$-$Z^2$. That is, -$Z^1$-$Z^2$ can be substituted at the two meta positions or the other ortho position with respect to the haloethylamino moiety. $Z^1$ is O, S, N($R^{11}$) in which $R^{11}$ is hydrogen or $C_{1-5}$ alkyl, or deleted. $Z^2$ is $C_{1-18}$ alkyl, $C_{3-10}$ cycloalkyl, 3- to 10-membered heterocycloalkyl, $C_{6-12}$ aryl, 5- to 12-membered heteroaryl, $C_{1-5}$ alkyl($C_{3-10}$ cycloalkyl), $C_{1-5}$ alkyl(3- to 10-membered heterocycloalkyl), $C_{1-5}$ alkyl($C_{6-12}$ aryl), or $C_{1-5}$ alkyl(5- to 10-membered heteroaryl).

Each of the above-mentioned cycloalkyl, heterocycloalkyl, aryl, and heteroaryl moieties, independently, can also be optionally substituted with amine (i.e., —NR'$_2$), amide (i.e., —NR'—C(=O)R' or —C(=O)—NR'$_2$), cyano, carboxyl, ester (i.e., —O—C(=O)—$C_{1-5}$ alkyl or —C(=O)—O—$C_{1-5}$ alkyl), halo, hydroxy, nitro, oxo (e.g., cyclohexanonyl), sulfonyl (i.e., —SO$_2$—R'), sulfinyl (i.e., —SO—R'), sulfonamide (i.e., —SO$_2$—NR'$_2$ or —NR'—SO$_2$), thio (i.e., —SR'), $C_{1-5}$ alkyl, $C_{6-12}$ aryl, $C_{1-5}$ alkoxy, or $C_{1-5}$ haloalkyl; each R', independently, being hydrogen or $C_{1-5}$ alkyl.

Another aspect of this invention also relates to a bis (haloethyl)aminobenzene derivative. One and only one of the two ortho positions with respect to the bis(haloethyl) amino substituent of the benzene ring is substituted with —C(=O)—O—$R^1$—$R^2$. $R^1$ is $C_{1-5}$ alkyl, or deleted. $R^2$ is hydrogen, $C_{3-10}$ cycloalkyl, 3- to 10-membered heterocycloalkyl, $C_{6-12}$ aryl, 5- to 12-membered heteroaryl, or —N($R^3$)$R^4$ in which each of $R^3$ or $R^4$, independently, is hydrogen, $C_{1-5}$ alkyl, $C_{3-10}$ cycloalkyl, 3- to 10-membered heterocycloalkyl, $C_{6-12}$ aryl, or 5- to 12-membered heteroaryl.

The remaining ortho position with respect to the bis (haloethyl)amino moiety of the benzene ring is substituted with —(—O—$C_{1-5}$ alkyl)$_{2-5}$ or —$Y^1$—$Y^2$. $Y^1$ is O, S, N($R^5$) in which $R^5$ is hydrogen or $C_{1-5}$ alkyl, or deleted. $Y^2$ is $C_{1-18}$ alkyl, $C_{2-18}$ alkenyl, $C_{3-10}$ cycloalkyl, 3- to 10-membered heterocycloalkyl, $C_{6-12}$ aryl, 5- to 10-membered heteroaryl, $C_{1-5}$ alkyl($C_{3-10}$ cycloalkyl), $C_{1-5}$ alkyl(3- to 10-membered heterocycloalkyl), $C_{1-5}$ alkyl(5- to 10-membered heteroaryl), $C_{1-5}$ alkyl($C_{6-12}$ aryl).

At least one of the remaining positions of the benzene ring is substituted with -$Z^1$-$Z^2$ wherein $Z^1$ is O, S, N($R^{11}$) in which $R^{11}$ is hydrogen or $C_{1-5}$ alkyl, or deleted. $Z^2$ is $C_{1-10}$ alkyl, $C_{3-10}$ cycloalkyl, 3- to 10-membered heterocycloalkyl, $C_{6-12}$ aryl, 5- to 12-membered heteroaryl, $C_{1-5}$ alkyl($C_{3-10}$ cycloalkyl), $C_{1-5}$ alkyl(3- to 10-membered heterocycloalkyl), $C_{1-5}$ alkyl($C_{6-12}$ aryl), or $C_{1-5}$ alkyl(5- to 10-membered heteroaryl).

Each of the above-mentioned cycloalkyl, heterocycloalkyl, aryl, and heteroaryl moieties, independently, can also be optionally substituted with amine (i.e., —NR'$_2$), amide (i.e., —NR'—C(=O)R' or —C(=O)—NR'$_2$), cyano, carboxyl, ester (i.e., —O—C(=O)—$C_{1-5}$ alkyl or —C(=O)—O—$C_{1-5}$ alkyl), halo, hydroxy, nitro, oxo (e.g., cyclohexanonyl), sulfonyl (i.e., —SO$_2$—R'), sulfinyl (i.e., —SO—R'), sulfonamide (i.e., —SO$_2$—NR'$_2$ or —NR'—SO$_2$), thio (i.e., —SR'), $C_{1-5}$ alkyl, $C_{6-12}$ aryl, $C_{1-5}$ alkoxy, or $C_{1-5}$ haloalkyl; each R', independently, being hydrogen or $C_{1-5}$ alkyl.

Some examples of the bis(haloethyl)aminobenzene derivatives of this invention are 2"-[(N,N-dimethyl)amino]-ethyl 4-bis(2'-chloroethyl)amino-3-butoxybenzoate, 4-bis (2'-chloroethyl)amino-3-butoxybenzoic acid, benzyl 3-cyclopropylmethoxy-4-bis(2'-chloroethyl)aminobenzoate, 2-bis[(2'-chloroethyl)]amino-3,5-dimethylbenzoic acid, and methyl 2-bis[(2'-chloroethyl)]amino-3,5-dimethylbenzoate.

A salt of a bis(haloethyl)aminobenzene derivative described above is also within the scope of this invention. For example, a salt can be formed between a positively charged amino substituent of the derivative and a negatively charged counterion. Suitable counterions include, but are not limited to, chloride, hydrochloride, bromide, iodide, sulfate, nitrate, phosphate, or acetate. Likewise, a negatively charged substituent, e.g., carboxylate, can form a salt with a cation such as an alkali metal cation (e.g., a sodium ion or a potassium ion); an alkaline earth metal cation (e.g., a magnesium cation or a calcium cation); or an ammonium cation optionally substituted with one or more organic groups (e.g., tetramethylammonium ion or diisopropylethylammonium ion).

The term "alkyl" in this disclosure denotes a straight or branched hydrocarbon group. Examples of alkyl include, but are not limited to, methyl, ethyl, propyl, isopropyl, butyl, isobutyl, sec-butyl, tert-butyl, amyl, and isopentyl.

"Cycloalkyl" is a cyclic hydrocarbon group. It may contain fused aliphatic rings, i.e., aliphatic rings that share a common carbon—carbon bond. Examples of cycloalkyl include, but are not limited to, cyclopropyl, cyclopentyl, cyclohexyl, cycloheptyl, norbornyl, and isobornyl.

"Heterocycloalkyl" is a cyclic hydrocarbon group that contains 1–3 heteroatoms such as nitrogen, oxygen, or sulfur and may also contain fused rings. By a "3-membered" heterocycloalkyl is meant a cyclic group containing 3 ring atoms. Some examples of heterocycloalkyl are tetrahydrofuranyl, tetrahydropyranyl, piperidinyl, morpholino and pyrrolindinyl groups.

By the term "alkenyl" is meant a straight or branched hydrocarbon chain and is characterized by having one or more double bonds. Typical alkenyl groups include allyl, 2-butenyl, 2-pentenyl, and 2-hexenyl.

"Aryl" is a cyclic aromatic moiety which may contain fused rings, e.g., an aromatic ring that shares a common carbon—carbon bond with an aliphatic ring (e.g., a cycloalkyl or a heterocycloalkyl) or with another aromatic ring, i.e., an aryl. Typical aryl groups include phenyl, 1-naphthyl, 2-naphthyl, and 1,2,3,4-tetrahydroisoquinolinyl. "Heteroaryl" refers to aryl groups that contain 1–3 heteroatoms. Some examples of heteroaryl are coumarinyl, pyridyl, pyrazinyl, pyrimidyl, furyl, pyrrolyl, thienyl, thiazolyl, oxazolyl, imidazolyl, indolyl, benzofuranyl, and benzthiazolyl. Similar to aryl, heteroaryl may contain fused aliphatic or aromatic rings.

"—(—O—$C_{1-5}$ alkyl)$_{2-5}$" refers to chain of 2–5 alkoxy groups. Each of the alkyl groups may or may not be identical. An example of an oligoalkylene glycol is ethoxymethoxy.

A further aspect of this invention relates to a composition which contains a bis(haloethyl)aminobenzene derivative (or its salt) described above and a pharmaceutically acceptable carrier. The derivative is in an amount which is effective for treating tumors. Still another aspect of this invention relates to a method of treating tumor, which comprises administering to a patient in need thereof an effective amount of such a bis(haloethyl)aminobenzene derivative or its salt. The use of such a bis(haloethyl)aminobenzene derivative for the manufacture of a medicament for treating tumors is also within the scope of this invention.

Unless otherwise defined, all technical and scientific terms used therein have the same meaning as commonly understood by one of ordinary skill in the art to which this invention belongs. Although methods and materials similar or equivalent to those described herein can be used in the practice or testing of the present invention, suitable methods and materials are described below. All publications cited herein are incorporated by reference in their entirety. In case of conflict, the present specification, including definitions, will control. In addition, the materials, methods, and examples are illustrative only and not intended to be limiting.

Other features or advantages of the present invention will be apparent from the following detailed description of several embodiments, and also from the appending claims.

DETAILED DESCRIPTION OF THE INVENTION

The present invention relates to a bis(haloethyl)amino benzene derivative or a salt thereof. Such a derivative can be used for treating tumor.

There exists many routes in the preparation of a bis (haloethyl)aminobenzene derivative of this invention. One can start with 3-hydroxy-4-nitrobenzoate. A substituent at the ortho-position with respect to the bis(haloethyl)amino moiety can be first introduced. As an example, 3-hydroxy-4-nitrobenzoate can react with a haloalkyl compound in a nucleophilic substitution reaction, resulting in the 3-hydroxyl group displacing the halo group of the haloalkyl compound. The displacement leads to the formation of an alkoxy substituent. See Example 2 below. The nitro group can then be reduced by a reducing agent, e.g., 10% Pd—C in methanol, to form an amino group, which can further react with an ethylene oxide to form a bis(hydroxyethyl)amino moiety. The bis(hydroxy-ethyl)amino moiety is then converted to a bis(haloethyl)-amino moiety by reagents such as thionyl chloride, phosphorus tribromide, or phosphorus/iodine. Hydrolysis of 3-alkoxy-4-(haloethyl)aminobenzoate converts the ester group to a carboxylate, which can be esterified to form a different ester group. See Example 4 below.

The order of introducing substituents to the benzene ring can be different from the method described above. For example, to prepare methyl 2-bis(2'-chloroethyl)amino-3,5-dimethylbenzoate, one can first reduce 2,4-dimethylnitrobenzene to 2,4-dimethylaniline, followed by introducing an ester group to the benzene ring via a reaction such as Friedel-Crafts acylation. Finally, the amino group of the benzene ring can be converted to a bis(chloroethyl) amino group using the above-described method.

A pharmaceutical composition containing a bis(haloethyl) aminobenzene derivative of this invention or its salt in an effective amount can be used to treat tumors. Some examples of tumors which can be treated by such a pharmaceutical composition are leukemia, lung cancer, colon cancer, CNS cancer, melanoma, ovarian cancer, cervical cancer, renal cancer, prostate cancer, and breast cancer. An effective amount of a bis(haloethyl)amino derivative or a salt thereof is defined as the amount which, upon administration to a patient in need, confers a therapeutic effect on the patient. The effective amount to be administered to a patient is typically based on age, surface area, weight, and conditions of the patient. The interrelationship of dosages for animals and humans (based on milligrams per meter squared of body surface) is described by Freireich et al., Cancer Chemother. Rep. 1966, 50, 219. Body surface area may be approximately determined from height and weight of the patient. See, e.g., Scientific Tables, Geigy Pharmaceuticals, Ardley, N.Y., 1970, 537. An effective amount of bis (haloethyl)amino derivative can range from about 0.1 mg/kg to about 250 mg/kg. Effective does will also vary, as recognized by those skilled in the art, dependant on route of administration, excipient usage, and co-usage with a different therapeutic treatment such as chemotherapy with another antitumor compound or radiation therapy.

The pharmaceutical composition may be administered via the parenteral route, e.g., orally, topically, subcutaneously, intraperitoneally, intramuscularly, or intravenously. Examples of parenteral dosage forms include aqueous solutions of the active agent, in an isotonic saline, 5% glucose or other well-known pharmaceutically acceptable excipient. Solubilizing agents, e.g., cyclodextrins, can be utilized as pharmaceutical excipients for delivery of the compositions.

The bis(haloethyl)aminobenzene derivative of this invention can also be formulated into dosage forms for other routes of administration utilizing conventional methods. A pharmaceutical composition can be formulated, for example, in dosage forms for oral administration in a capsule, a gel seal or a tablet. Capsules may comprise any standard pharmaceutically acceptable material such as gelatin or a cellulose derivative. Tables may be formulated in accordance with the conventional procedure by compressing mixtures of a bis(haloethyl)aminobenzene derivative of this invention and a solid carrier, and a lubricant. Examples of solid carriers include starch and sugar bentonite. The bis (haloethyl)aminobenzene derivative can also be administered in a form of a hard shell tablet or capsule containing, e.g., lactose or mannitol as a binder, a conventional filler and a tableting agent.

The antitumor activity of a bis(haloethyl)aminobenzene derivative of this invention can be preliminarily evaluated by using a tumor growth regression assay which assesses the ability of a tested compound to inhibit the growth of established solid tumors in mice. The assay can be performed by implanting tumor cells into the fat pads of nude mice. Tumor cells are then allowed to grow to a certain size before a bis(haloethyl)aminobenzene derivative is administered. The volumes of tumor are then monitored for a set number of weeks, e.g., three weeks. General health of the tested animals are also monitored during the course of the assay. The results of these in vivo tests can then be compared to those obtained by administering a known antitumor compound.

The following specific examples, which describe preparations and biological testings of bis(haloethyl) aminobenzene derivatives, are to be construed as merely illustrative, and not limitative of the remainder of the disclosure in any way whatsoever.

EXAMPLE 1

4-Bis(2'-chloroethyl)amino-3-(2'-(2''-methoxyethoxy)-ethoxy)benzoic Acid

A slurry of methyl 3-hydroxy-4-nitrobenzoate (5.5 g, 0.028 mol), 1-bromo-2-(2-methoxyethoxy)ethane (10.0 g, 0.055 mol) and potassium carbonate (20 g) in 100 mL dimethylformamide (DMF) was stirred at 90–100° C. for 2 hours. The reaction mixture was cooled to room temperature, diluted with 400 mL $H_2O$. The resulting solid was collected by filtration, washed with 100 mL $H_2O$, and dried to give methyl 3-(2'-(2''-methoxyethyl)ethoxy)-4-nitrobenzoate as a white solid (6.2 g, 74%). $^1$H NMR (300 MHz, $CDCl_3$): 7.82 (d, J=8.1 Hz, 1H), 7.78 (d, J=1.2 Hz, 1H), 7.69 (dd, J=8.1, 1.2 Hz, 1H, 4.33 (t, J=4.5 Hz, 2H), 3.95 (s, 3H, 3.92 (t, d, J=4.8 Hz, 2H), 3.73 (m, 2H), 3.55 (m, 2H), 3.38 (s, 3H). ESMS calcd ($C_{13}H_{17}NO_7$): 299.1; found: 300.1 $(M+H)^+$.

A methanol solution (200 mL) of methyl 3-(2'-(2''-methoxyethoxy)ethoxy)-4-nitrobenzoate (6.0 g, 0.020 mol) was stirred at room temperature in the presence of 10% Pd—C and 10 mL acetic acid under $H_2$ atmosphere for 20 hours. The reaction mixture was filtered through celite, concentrated to give methyl 4-amino-3-()2'-(2''-methoxyethoxy)ethoxy)benzoate as an off-white solid (5.0 g, 93%). $^1$H NMR (300 MHz, $CDCl_3$): 7.55 (d, J=8.7, 2.4 Hz, 1H), 7.47 (d, J=1.8 Hz, 1H), 6.67 (d, J=8.7 Hz, 1H), 4.22 (t, J=4.8 Hz, 2H), 3.87 (m, 2H), 3.85 (s, 3H), 3.70 (t, J=4.8 Hz, 2H), 3.58 (t, J=4.8 Hz, 2H), 3.39 (s, 3H). MS calcd ($C_{13}H_{29}NO_5$): 269.1; found: 270.1 $(M+H)^+$.

Methyl 4-amino-3-(2'-(2''-methoxyethoxy)ethoxy) benzoate (5.0 g, 18.6 mmol) and ethylene oxide (8.8 g, 200 mol) were dissolved in 150 mL acetic acid to form a reaction mixture. The mixture was stirred at room temperature for 12 hours. It was then diluted with 300 mL $H_2O$, extracted with chloroform/methanol (95/5, 4×200 mL). The organic solution was concentrated to form methyl 4-bis(2'-hydroxyethyl)amino-3-(2'-(2''-methoxyethoxy)ethoxy)benzoate as an off-white oil (6.1 g, 92%). $^1$H NMR (300 MHz, $CDCl_3$): 7.62 (dd, J=8.1, 2.1 Hz, 1H), 7.52 (d, J=2.1 Hz, 1H), 7.05 (d, J=7.2 Hz, 1H), 4.22 (m, 4H), 3.89 (s, 3H, 3.9–3.8 (m, 4H), 3.68 (m, 6H), 3.58 (m, 2H), 3.38 (m, 2H), 3.37 (s, 1H). ESMS calcd ($C_{17}H_{27}NO_7$): 357.2; found: 358.3 $(M+H)^+$.

Thionyl chloride (5.1 mL, 68 mmol) was added slowly to a solution of methyl 4-bis(2'-hydroxyethyl)amino-3-(2'-(2''-methoxyethoxy)ethoxy)benzoate (5.0 g, 13.3 mol) in benzene (100 mL) at room temperature. The reaction mixture was then stirred for 16 hours at the same temperature. It was then treated with ice/$H_2O$ (500 mL) and extracted with ethyl acetate (2×300 mL). The combined ethyl acetate solution was washed with sodium bicarbonate (20 mL), $H_2O$ (50 mL), dried over sodium sulfate, and concentrated to form methyl 4-bis(2'-chloroethyl)amino-3-(2'-(2''-methoxyethoxy)ethoxy)benzoate as an off-white oil (3.9 g, 74%). $^1$H NMR (300 MHz, $CDCl_3$): 7.58 (dd, J=8.7, 2.1 Hz, 1H), 7.49 (d, J=2.1 Hz, 1H), 6.88 (d, J=8.1 Hz, 1H), 4.18 (m, 2H), 3.87 (m, 2H), 3.86 (s, 3H), 3.69 (m, 2H), 3.36 (m, 8H), 3.56 (m, 2H), 3.37 (s, 3H). ESMS calcd ($C_{17}H_{25}Cl_2NO_5$): 393.1; found: 394.2 $(M+H)^+$.

A suspension of methyl 4-bis(2'-chloroethyl)amino-3-(2'-(2''-methoxyethoxy)ethoxy)benzoate (3.0 g, 7.64 mmol) in concentrated HCl (37% w/w in $H_2O$, 50 mL) was heated to refluxing under $N_2$ for 2 hours. The reaction mixture was treated with ice/$H_2O$ (100 mL), extracted with chloroform (2×100 mL). The organic extract was concentrated to give methyl 4-bis(2'-chloroethyl)amino-3-(2'-(2''-methoxyethoxy)ethoxy)benzoic acid as a white solid (2.8 g, 97%). $^1$H NMR (300 MHz, $CDCl_3$): 7.68 (dd, J=8.4, 2.1 Hz, 1H), 7.55 (d, J=2.1 Hz, 1H), 6.92 (d, J=8.7 Hz, 1H), 4.22 (m, 1H), 3.89 (m, 2H), 3.67 (m, 10H), 3.62 (m, 2H), 3.39 (s, 3H). ESMS calcd for $C_{16}H_{23}Cl_2NO_65$: 379.1; Found: 408.2 $(M-H)^+$.

EXAMPLE 2

4-Bis(2'-chloroethyl)amino-3-octoxybenzoic Acid

A slurry of methyl 3-hydroxy-4-nitrobenzoate (5.5 g, 0.028 mol), iodooctane (10.0 g, 0.042 mol) and potassium carbonate (20 g) in 100 mL DMF was stirred at 100° C. for 3 hours. The reaction mixture was cooled to room temperature, diluted with 500 mL $H_2O$, then extracted with ether/ethyl acetate (9/1, 2×200 mL). The combined organic solution was washed with 400 mL $H_2O$, dried over sodium sulfate, and concentrated to form methyl 4-nitro-3-octoxybenzoate as an off-white oil (8.7 g, 100%).

Methyl 4-nitro-3-octoxybenzoate (8.7 g, 0.028 mol) was dissolved in 150 mL methanol to form a solution. It was stirred at room temperature in the presence of 10% Pd—C under $H_2$ atmosphere for 29 hours. The reaction mixture was filtered through celite, concentrated to give the product methyl 4-amino-3-octoxybenzoate as an off-white solid (7.6 g, 96%). $^1$H NMR (300 MHz, $CDCl_3$): 7.25 (d, J=2.1 Hz, 1H), MS calcd ($C_{16}H_{25}NO_3$): 279.2; found: 279.0.

Methyl 4-amino-3-octoxybenzoate (3.47 g, 12.4 mmol) and ethylene oxide (4.5 g, 198 mol) were dissolved in 100 mL acetic acid to form a reaction mixture. The mixture was stirred at room temperature for 12 hours. It was then diluted with $H_2O$ (500 mL), extracted with chloroform/methanol (95/5, 4×100 mL). The organic extract was concentrated to brown oil. Flash chromatographic purification (silica gel, 5% to 10% methanol in chloroform) afforded the intermediate methyl 4-bis(2'-hydroxyethyl)amino-3-octoxybenzoate as an off-white oil (2.25 g, 42%). $^1$H NMR (300 MHz, $CDCl_3$): 7.62 (dd, J=8.1, 2.1 Hz, 1H), 7.55 (d, J=2.1 Hz, 1H), 7.12 (d, J=8.4 Hz, 1H), 4.06 (t, J=6.9 Hz, 2H), 3.90 (s, 3H), 3.64 (t, J=5.1 Hz, 4H), 3.38 (t, J=5.1 Hz, 4H), 1.86 (J=5.1 Hz, 2H), 1.30 (m, 10H), 0.89 (t, J=6.9 Hz, 3H). ESMS calcd ($C_{20}H_{33}NO_5$): 367.2; found: 390.3 $(N+Na)^+$.

Thionyl chloride (1.2 mL, 16 mmol) was added slowly to a solution of methyl 4-bis(2'-hydroxyethyl)amino-3-octoxybenzoate (2.20 g, 6.0 mol) in 50 mL benzene at room temperature. The reaction mixture was refluxed for 1.5 hours and then cooled to room temperature, treated with ice/$H_2O$ (100 mL), and extracted with ethyl acetate (50 mL). The organic extract was washed with sodium bicarbonate (20 mL), $H_2O$ (50 mL), dried over magnesium sulfate, and concentrated to furnish methyl 4-bis(2'-chloroethyl)amino-3-octoxybenzoate as an off-white oil (2.1 g, 87%). $^1$H NMR (300 MHz, $CDCl_3$): 7.58 (dd, J=8.1, 1.8 Hz, 1H), 7.51 (d, J=1.8 Hz, 1H), 6.92 (d, J=8.1 Hz, 1H), 4.03 (t, J=6.6 Hz, 1H), 3.89 (s, 3H), 3.60 (m, 8H), 1.85 (J=7.2 Hz, 2H), 1.30 (m, 10H), 0.89 (t, J=6.9 Hz, 3H). ESMS calcd ($C_{20}H_{31}Cl_2NO_3$): 403.2; found: 404.2 $(M+H)^+$.

A suspension of methyl 4-bis(2'-chloroethyl)amino-3-octoxybenzoate (1.8 g, 4.5 mmol) in concentrated HCl (37% w/w in $H_2O$, 50 mL) was heated to refluxing under $N_2$ for 0.5 hour. The reaction mixture was treated with ice/$H_2O$ (100 mL), extracted with chloroform (3×50 mL). The organic extract was concentrated to give a brown oil. Flash chromatographic purification (silica gel, 2% methanol in chloroform) gave the product 4-bis(2'-chloroethyl)amino-3-octoxybenzoic acid as an off-white solid (1.58 g, 88%). $^1$H NMR (300 MHz, $CDCl_3$): 7.67 (dd, J=8.1, 1.5 Hz, 1H), 7.56 (d, J=1.5 Hz, 1H), 6.93 (d, J=8.4 Hz, 1H), 4.40 (d, J=6.6 Hz, 2H), 3.65 (m, 8H), 1.85 (J=7.8 Hz, 2H), 1.35 (m, 10H), 0.90 (t, J=6.6 Hz, 3H). ESMS calcd ($C_{29}H_{29}Cl_2NO_3$): 389.2; found: 390.2 $(M+H)^+$.

EXAMPLE 3

2-Bis(2'-chloroethyl)amino-3,5-dimethylbenzoic Acid

Methyl 2-amino-3,5-dimethylbenzoate (7.0 g, 0.039 mol) and ethylene oxide (10 g, 0.23 mol) were dissolved in 150 mL acetic acid to form a reaction mixture. The mixture was stirred at room temperature for 19 hours. and then concentrated to about 100 mL on a rotary evaporator, diluted with $H_2O$ (300 mL), and extracted with chloroform (5×200 mL). The organic extract was concentrated to give the intermediate methyl 2-bis(2'-hydroxyethyl)amino-3,5-dimethylbenzoate as an off-white oil (10.0 g, 96%). $^1$H NMR (300 MHz, $CDCl_3$): 7.31 (br s, 1H), 7.16 (br s, 1H), 3.91 (s, 3H), 3.73 (m, 2H), 3.63 (m, 2H), 3.26 (br m, 4H), 2.32 (s, 3H), 2.30 (s, 3H).

Thionyl chloride (12 mL, 0.16 mol) was added slowly to a solution of methyl 2-bis(2'-hydroxyethyl)amino-3,5-dimethylbenzoate (7.0 g, 0.026 mol) in 200 mL benzene at room temperature. The reaction mixture was then stirred at room temperature for 12 more hours, and then treated with ice/$H_2O$ (500 mL) and extracted with ethyl acetate (2×300 mL). The extract was washed with $H_2O$ (300 mL), saturated sodium bicarbonate (200 mL), dried over magnesium sulfate, and concentrated to afford methyl 2-bis(2'-chloroethyl)amino-3,5-dimethylbenzoate as a clear oil (5.6 g, 71%). $^1$H NMR (300 MHz, $CDCl_3$): 7.31 (d, J=2.1 Hz, 1H), 7.17 (d, J=2.1 Hz, 1H), 3.88 (s, 3H), 3.53 (m, 4H), 3.37 (br m, 4H), 2.35 (s, 3H), 2.30 (s, 3H). ESMS calcd ($C_{14}H_{19}Cl_2NO_2$): 303.1; found: 304.1 $(M+H)^+$.

A suspension of methyl 2-bis(2'-chloroethyl)amino-3,5-dimethylbenzoate (5.6 g, 0.018 mol) in concentrated HCl (37% w/w in $H_2O$, 150 mL) was heated to refluxing under $N_2$ for 8 hours. The reaction mixture was treated with ice/$H_2O$ (200 mL), extracted wit chloroform (3×150 mL). The organic solution was concentrated to given the product 2-bis(2'-chloroethyl)amino-3,5-dimethylbenzoic acid as a white solid (5.1 g, 96%). $^1$H NMR (300 MHz, $CDCl_3$): 8.01 (d, J=1.5 Hz, 1H), 7.23 (dd, J=1.5, 0.6 Hz, 1H), 3.6 (m, 8H), 2.43 (s, 3H), 2.35 (s, 3H). ESMS calcd ($C_{13}H_{17}Cl_2NO_2$): 289.1; found: 290.1 $(M+H)^+$.

EXAMPLE 4

Benzyl 2-Bis(2'-chloroethyl)amino-3,5-dimethylbenzoate

2-Bis(2'-chloroethyl)amino-3,5-dimethylbenzoic acid (1.0 g, 3.45 mmol), benzyl alcohol (0.75 g, 6.90 mmol), 1,3-dicyclohexylcarbodiimide (0.82 g, 3.975 mmol), and 4-dimethylaminopyridine (0.50 g, 4.03 mmol) were dissolved in 25 mL dichloromethane at room temperature to form a reaction mixture. The mixture was stirred for 17 hours, diluted with hexanes (10 mL), cooled in the freezer for 20 minutes, and then filtered, It was then concentrated and then subjected to flash chromatographic purification (silica gel, 5% to 10% ethyl acetate in hexanes) to afford the product as a white oil (1.20 g, 92%). $^1$H NMR (300 MHz, $CDCl_3$): 7.4 (m, 5H), 7.33 (d, J=2.1 Hz, 1H), 7.17 (d, J=2.1 Hz, 1H), 5.32 (s, 2H), 3.46 (m, 4H), 3.30 (br m, 4H), 2.33 (s, 3H), 2.29 (s, 3H). ESMS calcd ($C_{20}H_{23}Cl_2NO_3$): 379.1; found: 380.2 $(M+H)^+$.

Examples 5–18 below provide NMR and mass spectrometry data of various bis(haloethyl)aminobenzene derivatives which were synthesized following procedures similar to those described in Examples 1–4.

EXAMPLE 5

4-[Bis-()2-chloroethyl)amino]-3-hexadecyloxybenzoic Acid Methyl Ester $^1$H NMR (300 MHz, $CDCl_3$): 7.58 (dd, 8.4 and 2.1 Hz, 1H), 7.51 (d, J=2.1 Hz, 1H), 6.91 (d, J=8.1 Hz, 1H), 4.03 (t, J=4.6 Hz, 2H), 3.88 (s, 3H), 3.60 (m, 8H), 1.84 (m, 2H), 1.48 (m, 2H), 1.26 (m, 24H), 0.88 (t, J=7.2 Hz, 3H). ESMS calcd ($C_{19}H_{30}Cl_2N_2O_3$): 515.2; found 516.3 $(M+H)^+$.

EXAMPLE 6

4[Bis-(2-chloroethyl)amino]-3-butoxybenzoic Acid $^1$H NMR (300 MHz, $CDCl_3$): 7.58 (dd, J=8.4, 2.1 Hz, 1H), 7.51 (d, J=1.8 Hz, 1H), 6.90 (d, J=8.4 Hz, 1H), 4.36 (t, J=6.3 Hz, 2H), 3.60 (m, 8H), 1.50 (m, 2H), 1.10 (m, 2H), 0.99 (t, J=7.5 Hz, 3H), ESMS calcd ($C_{15}H_{21}Cl_2NO_3$): 334.0; found: 335.1 $(M+H)^+$.

EXAMPLE 7

4-[Bis-(2-chloroethyl)amino]-3-hexadecyloxybenzoic Acid $^1$H NMR (300 MHz, $CDCl_3$): 7.54 (dd, 8.4, 2.1 Hz, 1H), 7.50 (d, J=2.1 Hz, 1H), 6.81 (d, J=8.1 Hz, 1H), 4.13 (t, J=4.6 Hz, 2H), 3.57 (m, 8H), 1.81 (m, 2H), 1.45 (m, 2H), 1.16 (m, 24H), 0.83 (t, J=7.2 Hz, 3H), ESMS calcd ($C_{27}H_{45}Cl_2NO_3$): 502.1; found: 503.2 $(M+H)^+$.

EXAMPLE 8

Benzyl 3-Cyclopropylmethoxy-4-bis(2'-chloroethyl) aminobenzoate $^1$H NMR (300 MHz, $CDCl_3$): 7.63 (dd, 8.4, 1.8 Hz, 1H), 7.49 (d, J=2.1 Hz, 1H), 7.4 (m, 5H), 6.88 (d, J=8.4 Hz, 1H), 5.34 (s, 2H), 3.86 (d, J=7.2 Hz 2H), 3.65 (s, 8H), 1.30 (m, 1H), 0.68 (m, 2H), 0.36 (m, 2H). ESMS calcd ($C_{22}H_{25}Cl_2NO_3$): 378.1; found: 379.2 $(M+H)^+$.

EXAMPLE 9

3-Benzyloxy-4-[bis-(2-chloroethyl)amino]benzoic Acid $^1$H NMR (300 MHz, $CDCl_3$): 7.62 (dd, J=8.4, 2.1 Hz, 1H), 7.49 (d, J=2.1 Hz, 1H), 7.30 (m, 5H), 6.92 (d, J=8.4 Hz, 1H), 5.20 (s, 2H), 3.61 (m, 8H). ESMS calcd ($C_{18}H_{19}Cl_2NO_3$): 168.0; found: 169.1 $(M+H)^+$.

EXAMPLE 10

3-Benzyloxy-4-[bis-(2-chloroethyl)amino]benzoic Acid Methyl Ester $^1$H NMR (300 MHz, $CDCl_3$): 7.62 (dd, J=8.4, 2.1 Hz, 1H), 7.49 (d, J=2.1 Hz, 1H), 7.30 (m, 5H), 6.92 (d, J=8.4 Hz, 1H), 5.20 (s, 2H), 3.90 (s, 3H), 3.61 (m, 8H). ESMS calcd ($C_{23}H_{21}Cl_2NO_3$): 430.1; found: 431.0 $(M+H)^+$.

EXAMPLE 11

4-[Bis-(2-chloroethyl)amino]-3-(furan-2-ylmethoxy)benzoic Acid $^1$H NMR (300 MHz, $CDCl_3$): 7.66 (dd, J=8.4, 2.1 Hz, 1H), 7.52 (d, J=2.1 Hz, 1H), 7.35 (s, 1H), 6.25 (d, J=7 Hz, 1H), 6.32 (d, J=7 Hz, 1H), 6.92 (d, J=84. Hz, 1H), 4.50 (s, 2H), 3.56 (m, 8H). ESMS calcd ($C_{16}H_{17}Cl_2NO_4$): 358.0; found: 359.1 $(M+H)^+$.

EXAMPLE 12

3-Cyclobutylmethoxy-4-bis-(2'-chloroethyl)aminobenzoic Acid $^1$H NMR (300 MHz, $CDCl_3$): 7.67 (dd, J=8.4, 2.1 Hz, 1H), 7.56 (d, J=2.1 Hz, 1H), 6.92 (d, J=8.4 Hz, 1H), 4.03 (d, J=6.9 Hz, 2H), 3.61 (m, 8H), 2.85 (m, 1H), 2.2 (m, 2H), 2.0–1.8 (m, 4H). ESMS calcd ($C_{16}H_{21}Cl_2NO_3$): 346.0; found: 347.1 $(M+H)^+$.

EXAMPLE 13

3-Cyclopropylmethoxy-4-bis-(2'-chloroethyl)aminobenzoic Acid $^1$H NMR (300 MHz, $CDCl_3$—$CD_3OD$): 7.68 (dd, J=8.1, 1.8 Hz, 1H), 7.60 (d, J=2.1 Hz, 1H), 7.41 (d, J=8.1 Hz, 1H), 3.97 (d, J=7.2 Hz, 2H), 3.87 (m, 4H), 3.65 (m, 4H), 1.3 (m, 1H), 0.68 (m, 2H), 0.38 (m, 2H). ESMS calcd ($C_{15}H_{19}Cl_2NO_3$): 332.0; found: 333.1 $(M+H)^+$.

EXAMPLE 14

Methyl 3-cyclopropylmethoxy-4-bis(2'-chloroethyl)aminobenzoate $^1$H NMR (300 MHz, $CDCl_3$): 7.58 (dd, J=8.4, 2.1 Hz, 1H), 7.45 (d, J=2.1 Hz, 1H), 6.88 (d, J=8.4 Hz, 1H), 3.89 (s, 3H), 3.87 (d, J=6.6 Hz, 2H), 3.65 (brs, 8H), 1.30 (m, 1H), 0.68 (m, 2H), 0.38 (m, 2H). ESMS calcd ($C_{16}H_{21}Cl_2NO_3$): 345.1; found: 346.0 $(M+H)^+$.

EXAMPLE 15

4-[Bis-(2-chloroethyl)amino]-3-isobutoxybenzoic Acid $^1$H NMR (300 MHz, $CDCl_3$): 7.67 (dd, J=8.4, 2.1 Hz, 1H), 7.53 (d, J=2.1 Hz, 1H), 6.90 (d, J=8.4 Hz, 1H), 3.61 (m, 8H), 3.40 (d, J=10 Hz, 2H), 1.55 (m, 1H), 1.22 (d, J=10 Hz, 6H) ESMS calcd ($C_{15}H_{21}Cl_2NO_3$): 334.0; found: 335.1 $(M+H)^+$.

EXAMPLE 16

Methyl 3-Cyclobutylmethoxy-4-bis-(2'-chloroethyl)aminobenzoate $^1$H NMR (300 MHz, $CDCl_3$): 7.58 (dd, J=8.4, 2.4 Hz, 1H), 7.51 (d, J=1.8 Hz, 1H), 6.90 (d, J=8.4 Hz, 1H), 4.01 (d, J=6.9 Hz, 2H), 3.89 (s, 3H), 3.60 (m, 8H), 2.84 (m, 1H), 2.20 (m, 2H), 2.1–1.8 (m, 4H). ESMS calcd ($C_{17}H_{23}Cl_2NO_3$): 359.1; found: 360.0 $(M+H)^+$.

EXAMPLE 17

4-[Bis-(2-chloroethyl)amino]-3-(3-methyl-but-2-enyloxy)benzoic Acid $^1$H NMR (300 MHz, $CDCl_3$): 7.71 (dd, J=8.4, 2.1 Hz, 1H), 7.56 (d, J=2.1 Hz, 1H), 6.91 (d, J=8.4 Hz, 1H), 5.40 (t, J=8 Hz, 1H), 4.21 (d, J=8 Hz, 2H), 3.61 (m, 8H), 1.72 (s, 3H), 1.75 (s, 3H) ESMS calcd ($C_{16}H_{21}Cl_2NO_3$): 346.0; found: 347.1 $(M+H)^+$.

EXAMPLE 18

4-[Bis-(2-chloroethyl)amino]-3-methoxybenzoic Acid $^1$N NMR (300 MHz, $CDCl_3$): 7.67 (dd, J=8.1, 1.5 Hz, 1H), 7.59 (d, J=1.5 Hz, 1H), 6.95 (d, J=8.1 Hz, 1H), 3.91 (s, 3H), 3.64 (m, 8H), ESMS calcd ($C_{12}H_{15}Cl_2NO_3$): 292.1; found: 293.2 $(M+H)^+$.

EXAMPLE 19

2'-(N,N-dimethylamino)ethyl 3-Butoxy-4-bis(2'-chloroethyl)aminobenzoate $^1$H NMR (300 MHz, $CDCl_3$): 7.58 (dd, J=8.4, 2.1 Hz, 1H), 7.51 (d, J=1.8 Hz, 1H), 6.90 (d, J=8.4 Hz, 1H), 4.36 (t, J=6.1 Hz, 2H), 4.02 (t, J=6.6 Hz, 2H), 3.60 (m, 8H), 3.54 (s, 6H), 2.84 (t, J=6.1 Hz, 2H), 2.63 (q, J=7.2 Hz, 4H), 1.82 (m, 2H), 1.50 (m, 2H), 1.10 (t, J=7.2 Hz, 6H), 0.99 (J=7.5 Hz, 3H) ESMS calcd ($C_{19}H_{30}Cl_2N_3O_3$): 404.2; found: 405.2 $(M+H)^+$.

EXAMPLE 20

Biological Testings

Human mammary carcinoma (MDA-35) tumor cells, which were adapted to grow as solid tumors in nude mice, were implanted by injection of a tumor cell suspension ($3–5 \times 10^6$ cells) in media into the fat pads of female nude mice (Taconic Labs). Five mice per group were used. When tumors were palpable, two to three weeks after implantation, animals were injected with the bis(haloethyl)aminobenzene derivatives of this invention intravenously on a three times per week schedule at the MTD. Tumor volumes were measured with calipers weekly during and for two weeks after dosing was suspended. The volume of tumors, assumed to be hemi-ellipsoid in shape, was calculated using the equation:

$$\text{Volume} = \frac{1}{2} (L/2 \times W/2 \times H)/3\pi$$

where L=length, W=width and H=height of the tumor. Animals were weighted and general health was monitored during the course of the assay. When tumors reached approximately 15 mm in diameter (about 800 mm$^3$) or necrotic or animals became moribund, the animals were euthanized by $CO_2$ asphyxiation.

The volumes of tumors in the animals which were treated with various bis-haloethyl)aminobenzene derivatives of this invention were calculated and compared to those obtained from the animals which were treated with chlorumbucil (an aromatic nitrogen mustard-containing anticancer drug) and also with those obtained from the untreated animals. Tested aminobenzene derivatives of this invention demonstrated unexpectedly high efficacy and stability in inhibiting tumor growth. For example, when an effective amount of 2"-[(N, N-dimethyl)amino]-ethyl 4-bis(2'-chloroethyl)amino-3-butoxybenzoate, 4-bis(2'-chloroethyl)amino-3-butoxybenzoic acid, benzyl 3-cyclopropylmethoxy-4-bis(2'-chloroethyl)-aminobenzoate, 2-bis[(2'-chloroethyl)]amino-3,5-dimethylbenzoic acid, or methyl 2-bis[(2'-chloroethyl)]-amino-3,5-dimethylbenzoate, was applied to the solid tumors in nude mice, the tumor sizes were reduced by 10–50 times as compared to those of mice which received no active antitumor agent (i.e., vehicles only); and was reduced by 8–40 times when compared to those of mice which received chlorumbucil for treatment.

Other Embodiments

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A bis(haloethyl)aminobenzene derivative wherein the para position with respect to the bis(haloethyl)amino substituent of the benzene is substituted with —C(=O)—O—R$^1$—R$^2$; R$^1$ being C$_{1-5}$ alkyl, or deleted; and R$^2$ being hydrogen, C$_{3-10}$ cycloalkyl, 3- to 10-membered heterocycloalkyl, C$_{6-12}$ aryl, 5- to 12-membered heteroaryl, or —N(R$^3$)R$^4$ in which each of R$^3$ and R$^4$, independently, is hydrogen, C$_{1-5}$ alkyl, C$_{3-10}$ cycloalkyl, 3- to 10-membered heterocycloalkyl, C$_{6-12}$ aryl, or 5- to 12-membered heteroaryl;

one and only one of the two ortho positions with respect to the bis(haloethyl)amino substituent of the benzene is substituted with C$_{2-18}$ alkyl, C$_{3-10}$ cycloalkyl, 3- to 10-membered heterocycloalkyl, C$_{6-12}$ aryl, 5- to 10-membered heteroaryl, C$_{1-5}$ alkyl(C$_{3-10}$ cycloalkyl), C$_{1-5}$ alkyl(3- to 10-membered heterocycloalkyl), C$_{1-5}$ alkyl(5- to 10-membered heteroaryl), C$_{1-5}$ alkyl(C$_{6-12}$ aryl), —(—O—C$_{1-5}$ alkyl)$_{2-5}$ or —Y$^1$—Y$^2$ in which Y$^1$ is O, S, or N(R$^5$) wherein R$^5$ is hydrogen or C$_{1-5}$ alkyl, and Y$^2$ is C$_{2-18}$ alkyl, C$_{2-18}$ alkenyl, C$_{3-10}$ cycloalkyl, 3- to 10-membered heterocycloalkyl, C$_{6-12}$ aryl, 5- to 10-membered heteroaryl, C$_{1-5}$ alkyl(C$_{3-10}$ cycloalkyl), C$_{1-5}$ alkyl(3- to 10-membered heteroaryl, C$_{1-5}$ alkyl(C$_{6-12}$ aryl), or C$_{1-5}$ alkyl(5- to 10-membered heteroaryl); and each of the remaining positions of the benzene, independently, is unsubstituted or substituted with -Z$^1$-Z$^2$; in which Z$^1$ is O, S, N(R$^{11}$) wherein R$^{11}$ is hydrogen or C$_{1-5}$ alkyl, or deleted, and Z$^2$ is C$_{1-18}$ alkyl, C$_{3-10}$ cycloalkyl, 3- to 10-membered heterocycloalkyl, C$_{6-12}$ aryl, 5- to 12-membered heteroaryl, C$_{1-5}$ alkyl (C$_{3-10}$ cycloalkyl), C$_{1-5}$ alkyl(3- to 10-membered heterocycloalkyl), C$_{1-5}$ alkyl(C$_{6-12}$ aryl), or C$_{1-5}$ alkyl (5- to 10-membered heteroaryl);

each cycloalkyl, heterocycloalkyl, aryl, and heteroaryl, independently, being optionally substituted with amine, amide, cyano, carboxyl, ester, halo, hydroxy, nitro, oxo, sulfonyl, sulfinyl, sulfonamide, thio, C$_{1-5}$ alkyl, C$_{6-12}$ aryl, C$_{1-5}$ alkoxy, or C$_{1-5}$ haloalkyl;

or a salt thereof.

2. The bis(haloethyl)aminobenzene derivative of claim 1, wherein the halo group is a chloro.

3. The bis(haloethyl)aminobenzene derivative of claim 1, wherein one of the ortho positions with respect to the bis(haloethyl)amino substituent of the benzene is substituted with —(—O—C$_{1-5}$ alkyl)$_{2-5}$; or a salt thereof.

4. The bis(haloethyl)aminobenzene derivative of claim 3, wherein R$^2$ is hydrogen, C$_{6-12}$ aryl, or —N(R$^3$)R$^4$, in which each of R$^3$ and R$^4$, independently, is hydrogen or C$_{1-5}$ alkyl; or a salt thereof.

5. The bis(haloethyl)aminobenzene derivative of claim 4, wherein each of the remaining positions of the benzene is unsubstituted; or a salt thereof.

6. The bis(haloethyl)aminobenzene derivative of claim 1, wherein Y$^1$ is O; or a salt thereof.

7. The bis(haloethyl)aminobenzene derivative of claim 6, wherein Y$^2$ is C$_{2-6}$ alkyl or C$_{1-5}$ alkyl(C$_{3-10}$ cycloalkyl); or a salt thereof.

8. The bis(haloethyl)aminobenzene derivative of claim 7, wherein Y$^2$ is butyl or methyl(cyclopropyl); or a salt thereof.

9. The bis(haloethyl)aminobenzene derivative of claim 8, wherein each of the remaining positions of the benzene is unsubstituted; or a salt thereof.

10. The bis(haloethyl)aminobenzene derivative of claim 8, wherein R$^1$ is C$_{1-2}$ alkyl, or deleted; and R$^2$ is hydrogen, phenyl, or —N(CH$_3$)$_2$; or a salt thereof.

11. The bis(haloethyl)aminobenzene derivative of claim 1, said derivative being 2"-[(N,N-dimethyl)amino]ethyl 4-bis(2'-chloroethyl)amino-3-butoxybenzoate, 4-bis (2'chloroethyl)amino-3-butoxybenzoic acid, or benzyl 3-cyclopropylmethoxy-4-bis(2'-chloroethyl) aminobenzoate; or a salt thereof.

12. The bis(haloethyl)aminobenzene derivative of claim 1, wherein R$^1$ is C$_{1-5}$ alkyl, or deleted, and R$^2$ is C$_{6-12}$ aryl, or —N(R$^3$)R$^4$ in which each of R$^3$ and R$^4$, independently, is hydrogen or C$_{1-5}$ alkyl; or a salt thereof.

13. The bis(haloethyl)aminobenzene derivative of claim 12, wherein R$^1$ is C$_{1-2}$ alkyl, or deleted; and R$^2$ is phenyl or —N(CH$_3$)$_2$; or a salt thereof.

14. The bis(haloethyl)aminobenzene derivative of claim 1, wherein each of the remaining positions of the benzene is unsubstituted; or a salt thereof.

15. A bis(haloethyl)aminobenzene derivative wherein one and only one of the two ortho positions with respect to the bis(haloethyl)amino substituent of the benzene is substituted with —C(=O)—O—R$^1$—R$^2$; R$^1$ being C$_{1-5}$ alkyl, or deleted; R$^2$ being hydrogen, C$_{3-10}$ cycloalkyl, 3- to 10-membered heterocycloalkyl, C$_{6-12}$ aryl, 5- to 12-membered heteroaryl, or —N(R$^3$)R$^4$ in which each of R$^3$ and R$^4$, independently, is hydrogen, C$_{1-5}$ alkyl, C$_{3-10}$ cycloalkyl, 3- to 10-membered heterocycloalkyl, C$_{6-12}$ aryl, or 5- to 12-membered heteroaryl;

the remaining ortho position with respect to the bis (haloethyl)amino substituent of the benzene is substituted with —(—O—C$_{1-5}$ alkyl)$_{2-5}$ or —Y$^1$—Y$^2$; Y$^1$ being O, S, N(R$^5$) in which R$^5$ is hydrogen or C$_{1-5}$ alkyl, or deleted; and Y$^2$ being C$_{1-18}$ alkyl, C$_{2-18}$ alkenyl, C$_{3-10}$ cycloalkyl, 3- to 10-membered heterocycloalkyl, C$_{6-12}$ aryl, 5- to 10-membered heteroaryl, C$_{1-5}$ alkyl(C$_{3-10}$ cycloalkyl), C$_{1-5}$ alkyl(3- to 10-membered heterocycloalkyl), $C_{1-5}$ alkyl(5- to 10-membered heteroaryl), $C_{1-5}$ alkyl($C_{6-12}$ aryl); and at least one of the remaining positions of the benzene is substituted with -$Z^1$-$Z^2$ in which $Z^1$ is O, S, N($R^{11}$) where $R^{11}$ is hydrogen or $C_{1-5}$ alkyl, or deleted, and $Z^2$ is $C_{1-10}$ alkyl, $C_{3-10}$ cycloalkyl, 3- to 10-membered heterocycloalkyl, $C_{6-12}$ aryl, 5- to 12-membered heteroaryl, $C_{1-5}$ alkyl($C_{3-10}$ cycloalkyl), $C_{1-5}$ alkyl(3- to 10-membered heterocycloalkyl), $C_{1-5}$ alkyl($C_{6-12}$ aryl), or $C_{1-5}$ alkyl(5- to 10-membered heteroaryl);

each cycloalkyl, heterocycloalkyl, aryl, and heteroaryl, independently, being optionally substituted with amine, amide, cyano, carboxyl, ester, halo, hydroxy, nitro, oxo, sulfonyl, sulfinyl, sulfonamide, thio, $C_{1-5}$ alkyl, $C_{6-12}$ aryl, $C_{1-5}$ alkoxy, or $C_{1-5}$ haloalkyl;

or a salt thereof.

16. The bis(haloethyl)aminobenzene derivative of claim 15, wherein the halo group is a chloro.

17. The bis(haloethyl)aminobenzene derivative of claim 15, wherein $R^1$ is $C_{1-2}$ alkyl, or deleted; and $R^2$ is hydrogen or phenyl; or a salt thereof.

18. The bis(haloethyl)aminobenzene derivative of claim 17, wherein $R^1$ is deleted and $R^2$ is hydrogen; or a salt thereof.

19. The bis(haloethyl)aminobenzene derivative of claim 15, wherein one and only one of the two ortho positions with respect to the bis(haloethyl)amino substituent of the benzene is substituted to $C_{1-5}$ alkyl; or a salt thereof.

20. The bis(haloethyl)aminobenzene derivative of claim 19, wherein at least one of the remaining positions of the benzene is substituted with -$Z^1$-$Z^2$ in which $Z^1$ is deleted, and $Z^2$ is $C_{1-5}$ alkyl; or a salt thereof.

21. The bis(haloethyl)aminobenzene derivative of claim 20, wherein -$Z^1$-$Z^2$ is at the para position with respect to the bis(haloethyl)amino substituent of the benzene; or a salt thereof.

22. The bis(haloethyl)aminobenzene derivative of claim 15, said derivative being 2-bis[(2'-chloroethyl)]amino-3,5-dimethylbenzoic acid or methyl 2-bis[(2'-chloroethyl)]amino-3,5-dimethylbenzoate; or a salt thereof.

23. The bis(haloethyl)aminobenzene derivative of claim 6, wherein $R^2$ is hydrogen, $C_{6-12}$ aryl, or —N($R^3$)$R^4$, in which each of $R^3$ and $R^4$, independently, is hydrogen or $C_{1-5}$ alkyl; or a salt thereof.

24. The bis(haloethyl)aminobenzene derivative of claim 7, wherein $Y^2$ is $C_{4-6}$ alkyl; or a salt thereof.

25. The bis(haloethyl)aminobenzene derivative of claim 1, wherein one of the ortho positions with respect to the bis(haloethyl)amino substituent of the benzene is substituted with —$Y^1$—$Y^2$ in which $Y^1$ is N($R^5$) wherein $R^5$ is hydrogen or $C_{1-5}$ alkyl, and $Y^2$ is $C_{1-18}$ alkyl, $C_{2-18}$ alkenyl, $C_{1-5}$ alkyl($C_{3-10}$ cycloalkyl), $C_{1-5}$ alkyl($C_{6-12}$ aryl), or $C_{1-5}$ alkyl (5- to 10-membered heteroaryl); or a salt thereof.

26. The bis(haloethyl)aminobenzene derivative of claim 25, wherein $R^2$ is hydrogen, $C_{6-12}$ aryl, or —N($R^3$)$R^4$, in which each of $R^3$ and $R^4$, independently, is hydrogen or $C_{1-5}$ alkyl; or a salt thereof.

27. The bis(haloethyl)aminobenzene derivative of claim 26, wherein each of the remaining positions of the benzene is unsubstituted; or a salt thereof.

28. The bis(haloethyl)aminobenzene derivative of claim 1, wherein $R^1$ is $C_{1-5}$ alkyl, or deleted, and $R^2$ is hydrogen; or a salt thereof.

29. The bis(haloethyl)aminobenzene derivative of claim 28, wherein $R^1$ is $C_{1-2}$ alkyl, or deleted; or a salt thereof.

30. The bis(haloethyl)aminobenzene derivative of claim 15, wherein one and only one of the two ortho positions with respect to the bis(haloethyl)amino substituent of the benzene is substituted with —$Y^1$—$Y^2$ in which $Y^1$ is O, and $Y^2$ is $C_{4-6}$ alkyl; or a salt thereof.

* * * * *